Nov. 18, 1975 A. W. FISCHER Plant Pat. 3,807
AFRICAN VIOLET ENTITLED
ULLI
Filed Dec. 18, 1974
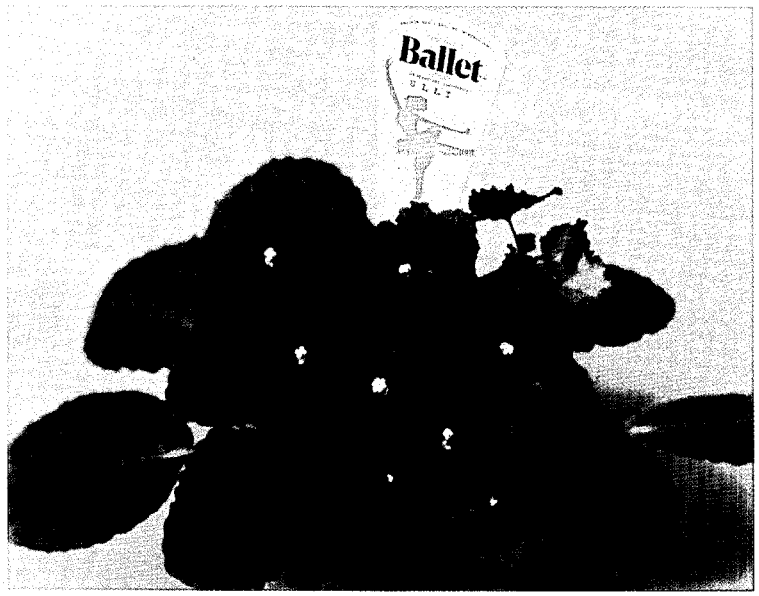
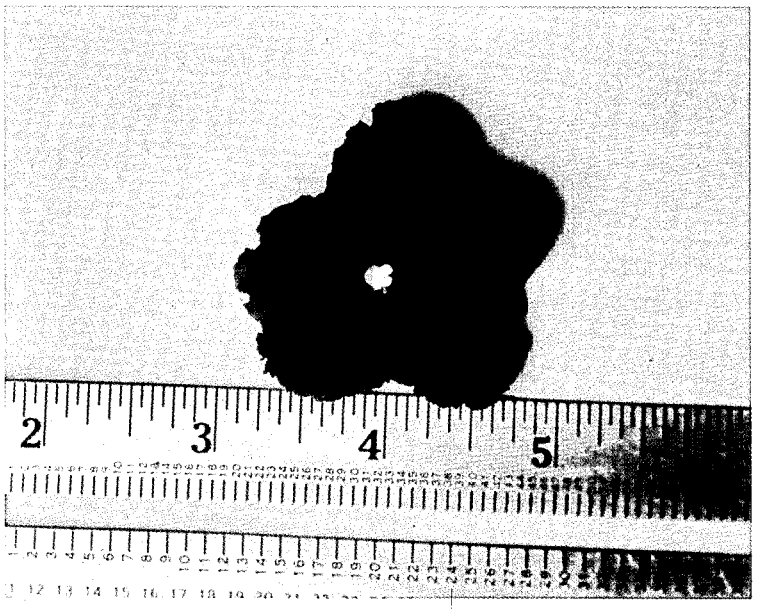

United States Patent

Plant Pat. 3,807

Patented Nov. 18, 1975

3,807

AFRICAN VIOLET

Arnold W. Fischer, Isernhagen, Germany, assignor to Geo. J. Ball, Inc., West Chicago, Ill.

Filed Dec. 18, 1974, Ser. No. 534,141

Int. Cl. A01h 5/00

U.S. Cl. Plt.—69 1 Claim

ABSTRACT OF THE DISCLOSURE

A new variety of African violet plant for potted plant culture particularly distinguished by its vigorous growing habit and a long lasting flowering cycle with a profuse production of large, well spaced blooms which are borne on upright stems and fully cover the center of the plant, the flowers being of an intense dark blue color enhanced by their bright yellow anthers.

BACKGROUND OF THE NEW PLANT

My new variety of African violet was orginated as a seedling by my crossing of two unnamed and unpatened plants selected by me from the stock of violet varieties kept by me at Isernhagen, Germany, for breeding purposes with the object of developing new and improved African violet plants for commercial exploitation.

This plant was selected by me for trial because of its condensed growth and profuse production of large blossoms borne on sturdy, upright stems and providing a full crown for the center of the plant. Asexual reproduction of this plant by means of leaf cuttings, carried on by me and under my direction through several generations at Isernhagen, Germany, has shown that its distinctive characteristics hold true from generation to generation and appear to be firmly fixed; and this new plant is now being propagated on a commercial scale, by leaf cuttings and division of roots, at West Chicago, Ill., U.S.A.

DESCRIPTION OF THE DRAWING

My new variety of African violet plant is illustrated by the accompanying photographic drawing in color which shows the form and size characteristics of the flowers of the plant, as well as its compact growth habit, the color rendition of the flowers being considerably lighter than the true dark purple-blue color in order to retain details of the blossoms that would be lost if the true color were to be sought by conventional photographic procedures. The upper view shows a typical plant of the new variety in full bloom. The lower view is a close-up picture of one of the blossoms showing its size and details of its form; and a general representation of the actual flower coloring is shown by the hand painted color swatch affixed to the drawing.

DESCRIPTION OF THE NEW PLANT

The following is a detailed description of my new varitey of African violet plant with color designations according to the Robert F. Wilson Horticultural Colour Chart (HCC) published by the British Colour Council in collaboration with The Royal Horticultural Society at London, England.

THE PLANT

Origin: Seedling.

Parentage:

*Seed parent.*—65–1 (unpatented).

*Pollen parent.*—X69–25 (unpatented).

These plants are unnamed varieties maintained by me for breeding purposes and are identified in my records by the above stated numbers.

Classification:

*Botanic.*—*Saintpaulia ionantha.*

*Commercial.*—African violet.

Form: Compact potted plant.

Height: 4 inches from base to top of flowers.

Growth: Condsensed and vigorous with sturdy upright flower peduncles and fairly strong petioles which tend to spread horizontally.

Foliage: Abundant.

*Size of leaf.*—About 3 inches long and 2½ to 3 inches wide when mature.

*Shape of leaf.*—Ovate to orbicular with crenate margins.

*Texture.*—Tomentose and leathery.

*Color.*—Upper side—Ivy Green 0001060/3. Under side—Lilac Purple 031/2 to 31 fluctuating to Carnation Green 00058 according to age of leaf.

*Ribs and veins.*—Pinnate—very pronounced on under side of leaf.

*Petioles.*—3 to 3½ inches long and fairly strong.

THE BUD

Form: Globular, becoming urn-shaped as it opens.

Size: ¼ inch in diameter.

Opening rate: Bud opens very slowly. 5 weeks from visible bud to opening of flower.

Color: When sepals unfurl—Violet 36 and Pastel Lilac 437/3 (in general representation).

Sepals: Hooded over bud for a very short period.

*Form.*—Spear shaped and upstanding.

*Color.*—Inside—Fern Green 0862/3. Outside—Lilac Purple 031/1.

Calyx:

*Shape.*—Synsepalous and funnel shaped.

*Splitting.*—Calyx splits to star-shape.

*Aspect.*—Hairy on outside, smooth on inside.

Pedicel:

*Length.*—1 to 2 inches.

*Aspect.*—Erect and tomentose.

*Color.*—Lilac Purple 031/1.

THE FLOWER

Blooming habit: Recurrent the year around and profuse.

Size of flower: Large. About 1½ to 2″ in diameter.

Shape of flower: When first opening—very open cup-shaped. As flower matures, it becomes quite flat.

Borne: The inflorescence is a cyme.

Petalage: Number of petals—5, three being larger than the remaining two.

*Form.*—Rotate with bilateral symmetry and wavy margins.

*Arrangement.*—Synpetalous.

*Color.*—The general color representation is Victoria Violet 738. Mature flower: Top side—Victoria Violet 738 to 738/3. Reverse side—Campanula Violet 37 to 37/1. Old flower: Top side—methyl Violet 39 to Aster Violet 38. Reserve side—Aster Violet 38 to Victoria Violet 738/1.

*Discoloration.*—After full bloom the color tends to fade.

*Texture.*—Soft.

*Appearance.*—Velvety. Glittery on the upper surface and satiny on under side.

Peduncle:

*Main stem.*—Sturdy and upright. Length—about 2 inches.

*Pedicels.*—About 1 to 1½ inches long, upright and strong.

*Color.*—Lilac Purple 031/1.

Effect of weather: Hot weather suppresses flowering and fades the color. Plants thrive best in 80 to 90% humidity.

Fragrance: None.
Persistence: Flowers hang on and dry.
Lasting quality: 10 to 14 days for the fully opened flowers.

REPRODUCTIVE ORGANS

Stamens:
*Filaments.*—3–16 inch long. Color: Petunia Purple 32/2.
*Anthers.*—Number—2; occasionally 3 or 4, each with anther cells of Sulphur Yellow 2 in color. Length: 3/32 inch. Arrangement: Basified.
*Pollen.*—Color—White.
Pistils: Number—One.
*Length of Style.*—5/16 inch.
*Stigma.*—Color—Cobalt Violet 634/2.
Ovaries: Superior and tomentose.

The principal advantageous characteristics of this new

African violet plant reside in its large, well spaced open blooms which are borne on upright stems, above outwardly spreading foliage, to fully cover the center of the plant; the intense dark blue coloring of the flowers; its vigorous growth habit; and the long-lasting flowering cycle.

I claim:

1. A new and distinct variety of African violet plant, substantially as herein shown and described, characterized by the large size of its dark blue flowers which are borne on sturdy upright stems and are well spaced to fully cover the center of the plant, its vigorous growth habit and profuse year around flowering, and its long-lasting flowering cycle.

No references cited.

ROBERT E. BAGWILL, Primary Examiner